United States Patent [19]

Schneider et al.

[11] 4,086,356
[45] Apr. 25, 1978

[54] FUNGICIDAL-N-(3-HALO-2,6-DINITRO-4-TRIFLUOROMETHYLPHENYL)-PYRROLIDONES

[75] Inventors: Louis Schneider, Elizabeth; David E. Graham, Westfield, both of N.J.

[73] Assignee: GAF Corporation, New York, N.Y.

[21] Appl. No.: 765,904

[22] Filed: Feb. 7, 1977

[51] Int. Cl.² ............... A61K 31/40; C07D 207/24; C07D 207/26
[52] U.S. Cl. .................... 424/274; 260/326.5 FL; 260/326.82
[58] Field of Search ............ 260/326.5 FL, 326.9, 260/326.82; 424/274

[56] References Cited

U.S. PATENT DOCUMENTS

| | | | |
|---|---|---|---|
| 2,916,498 | 12/1959 | Lutz et al. | 260/326.5 FL |
| 3,586,725 | 6/1971 | Hunter | 71/121 |
| 3,769,301 | 10/1973 | Olin | 260/326.45 |
| 3,966,816 | 6/1976 | Woods et al. | 260/293.72 |

*Primary Examiner*—Donald G. Daus
*Assistant Examiner*—Jose Tovar
*Attorney, Agent, or Firm*—Walter C. Kehm; Walter Katz

[57] ABSTRACT

Fungicidal-N-(3-halo-2,6-dinitro-4-trifluoromethylphenyl)-pyrrolidones having the formula:

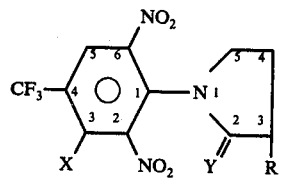

where
X is a halogen,
Y is oxygen or sulfur, and
R is H or lower alkyl, of up to 4 carbon atoms,
are prepared by reacting a 2,4-dihalo-3,5-dinitrobenzotrifluoride with an alkali metal salt of a pyrrolidone.

The compounds of the invention show good fungicidal activity, particularly against rice spot and tomato blight.

11 Claims, No Drawings

FUNGICIDAL-N-(3-HALO-2,6-DINITRO-4-TRI-FLUOROMETHYLPHENYL)-PYRROLIDONES

BACKGROUND OF THE DISCLOSURE

1. Field of the Invention

This invention relates to fungicidal compounds which are N-(substituted-phenyl)-pyrrolidones.

2. Description of the Prior Art

Aromatic compounds are known in the art as being useful agricultural chemicals. Accordingly, it is the object of this invention to provide new and useful compounds which exhibit good fungicidal activity.

SUMMARY OF THE INVENTION

The present invention provides fungicidal-N-(3-halo-2,6-dinitro-4-trifluoromethylphenyl)-pyrrolidones having the formula:

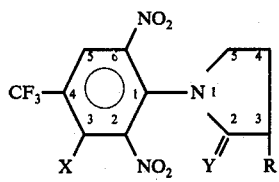

where
X is a halogen,
Y is oxygen or sulfur, and
R is H or lower alkyl, of up to 4 carbon atoms.

The compounds of this invention are prepared by reacting a 2,4-dihalo-3,5-dinitrobenzotrifluoride with an alkali metal salt of a pyrrolidone.

The N-(substituted-phenyl)-pyrrolidones described herein show good fungicidal activity, particularly against rice spot and tomato blight.

DESCRIPTION OF THE PREFERRED EMBODIMENTS

The compounds (III) of this invention are prepared by condensing a 2,4-dihalo-3,5-dinitrobenzotrifluoride (I) with an alkali metal salt of a pyrrolidone (II), as follows:

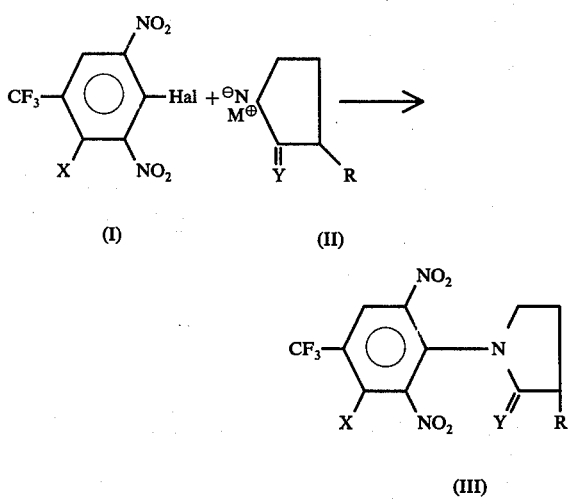

where Hal is a halogen, M+ is an alkali metal, and X, Y and R are as previously defined.

I is produced by dinitration of the corresponding dihalobenzotrifluoride compound in a mixture of nitric and sulfuric acids, as described in U.S. Pat. No. 3,586,725. II is prepared by reacting pyrrolidone with an alkali methoxide.

The condensation reaction is carried out by stirring the reactants for an extended period of time at room temperature, in a suitable solvent, and then at an elevated temperature for an additional period of time. Upon completion of the reaction, the solvent is removed and the desired product is separated by partition extraction. The extraction agent then is removed by rotoevaporation and the product is crystallized from a suitable solvent.

The compounds of this invention are especially useful as agricultural fungicides. Usually they are applied to the soil at the rate of about 1 to 25 lbs. per acre or as a foliar spray at concentrations of about 31 to 260 ppm. They show particularly effective foliar fungicidal activity against the following pathogens: blight of tomatoes and rice spot.

The materials of the present invention may be applied to those fungus susceptible plants on site at a rate of about 1 or less to about 25 pounds per acre depending on various circumstances of the susceptibility to the fungus, the weather, the stage of growth and various other factors. The material may be applied as a dust or spray. As a dust it is more practical to extend it with diluents such as bentonite, chalk, clay, diatomaceous earth, fullers earth, mica, ground slate or any of the other usual carriers for agricultural chemicals. As a spray it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the fungus.

The following are examples of preparation of representative compounds of the invention, and are presented by way of illustration, and are not intended to be limiting unless otherwise specified.

EXAMPLE 1

N-(3-Chloro-2,6-Dinitro-4-Trifluoromethylphenyl)-Pyrrolidone

Sodium methoxide (5.4 g., 0.1 mole) in 200 ml. of benzene is charged into a 500 cc 4-neck flask maintained under an atmosphere of nitrogen, and heated to 70° C. Pyrrolidinone (10.2 g., 0.12 mole) then is added during a period of 1 hour while maintaining the reactants at 70°–80° C. At the conclusion of the reaction period, 35 cc. of a benzene-methanol mixture is distilled off. 100 cc. of dimethylformamide and benzene is removed under vaccuum until the pot temperature reaches 80° C. 2,4-Dichloro-35-dinitrobenzotrifluoride (30.5 g., 0.1 mole) in 20 cc. of dimethylformamide is added to the residual material, namely, sodium salt of pyrrolidone, at room temperature. The mixture is stirred for 19 hours at room temperature, and then is heated at 75° C for 2 hours. The dimethylformamide solvent then is removed at 80° C under 1 mm. pressure. The residue is partitioned between toluene and water; the water-washed toluene layer separated, the toluene removed by rotoevaporation, and the product is crystallized twice from methanol. The yield is 3.5 g. (9%), m.p. 121°–122° C.

Anal. Calcd for Nitrogen: N,11.87; Found: 11.67, Calcd for Chlorine, 10.0; Found: 9.80.

EXAMPLE 2

N-(3-Halo-2,6-Dinitro-4-Trifluoromethylphenyl)-Thiopyrrolidone

The procedure of Example 1 is followed except that thiopyrrolidone (prepared as described in the literature* by reaction of pyrrolidone and phosphorous pentasulfide in refluxing benzene) is used in place of pyrrolidone, to provide the desired compound.

* Tafel et al., Ber. 40, 2842-48 (1907)

EXAMPLE 3

N-(3-Halo-2,6-Dinitro-4-trifluoromethylphenyl)-3-Butyl-Pyrrolidone

The procedure of Example 1 is followed except that 3-butylpyrrolidone (prepared as described in the literature* by reaction of pyrrolidone with 1-benzene in isopropanol with di-butyl peroxide as a catalyst at 35° C for 16 hours) is used in place of pyrrolidone, to provide the desired product.

* D. Elad and J. Sinnreich, Chemical Industry (London) 1965 (18), P. 768–9; 2) Nikishin, G. I. and Mustafaer, R. I., Chemical Abstracts 62, 2753 h (1965).

EXAMPLE 4

Foliar Fungicidal Tests

The product of Example 1 was tested on tomato early blight as follows: Young tomato seedlings 4 to 5 weeks of age were atomized while rotating on a turntable with a suspension of the test material diluted to 250 ppm. After the deposit dried, the plants were atomized with a spore suspension and incubated in a humidity cabinet at 70° to 75° F for 24 hours. Then they are held in a greenhouse until lesions appear (usually 2 to 3 days). The severity of infection is rated on a scale of 0 (no reduction) to 10 (complete elimination of infection). The results versus the standard Maneb, managanese ethyl bis-dithicarbamate, are as follows:

| Conc., ppm. | Fungitoxicity Rating | |
| --- | --- | --- |
| | Compound of Ex. 1 | Maneb |
| 250 | 8.0 | 9.5 |

EXAMPLE 5

The product of Example 1 was tested on rice leaf spot as follows: Young Star Bonnet rice plants about 2 weeks old growing in 2.5 inch pot were sprayed while rotating with a suspension containing 250 ppm. of material. After the spray deposit dried, the plants were atomixed with a conidial suspension and placed in a moist chamber at 75° F. for 24 hours to facilitate infection. After discrete lesions appeared in the unprotected controls (2 days), the infection was rated versus the commercial standard Maneb.

| Conc., ppm | Fungitoxicity Rating | |
| --- | --- | --- |
| | Compound of Ex. 1 | Maneb |
| 250 | 8.0 | 9.5 |

While the invention has been described with particular reference to certain embodiments thereof, it will be understood that certain modifications and changes may be made which are within the skill of the art. Therefore it is intended to be bound only by the appended claims.

What is claimed is:

1. N-(3-halo-2,6-dinitro-4-trifluoromethylphenyl)pyrrolidones having the formula:

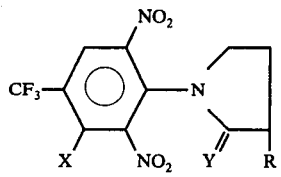

where
X is a halogen,
Y is oxygen or sulfur, and
R is H or lower alkyl, of up to 4 carbon atoms.

2. A compound according to claim 1 wherein X is chlorine.

3. A compound according to claim 1 wherein Y is oxygen.

4. A compound according to claim 1 wherein Y is sulfur.

5. A compound according to claim 1 wherein R is H.

6. A compound according to claim 1 wherein R is butyl.

7. A compound according to claim 1 which is N-(3-chloro-2,6-dinitro-4-trifluoromethylphenyl)-pyrrolidone.

8. A compound according to claim 1 which is N-(3-halo-2,6-dinitro-4-trifluoromethylphenyl)-thiopyrrolidione.

9. A compound according to claim 1 which is N-(3-halo-2,6-dinitro-4-trifluoromethylphenyl)-3-butylpyrrolidone.

10. A method of controlling undesired pathogens comprising applying thereto a fungicidally effective amount of a compound having the formula:

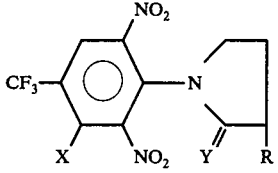

where
X is a halogen,
Y is oxygen or sulfur, and
R is H or lower alkyl, of up to 4 carbon atoms.

11. A fungicidal composition of matter comprising:
(a) a fungicidally effective amount of a N-(3-halo-2,6-dinitro-4-trifluoromethylphenyl)-pyrrolidone having the formula:

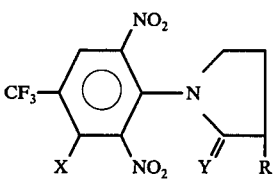

where
X is a halogen,
Y is oxygen or sulfur, and
R is H or lower alkyl, of up to 4 carbon atoms and
(b) an inert carrier.

* * * * *